(12) United States Patent
Nyholm et al.

(10) Patent No.: US 7,542,545 B2
(45) Date of Patent: Jun. 2, 2009

(54) METHOD AND DEVICE FOR CALCULATING THE RADIATION DOSE DISTRIBUTION FOR A RADIATION TREATMENT SYSTEM FOR THE PURPOSE OF RADIATION THERAPY OF AN ANIMAL BODY

(75) Inventors: Tufve Nyholm, Umea (SE); Jorgen Olofsson, Umea (SE); Anders Ahnesjo, Uppsala (SE); Mikael Karlsson, Tavelsjo (SE)

(73) Assignee: Nucletron B.V., Veenendaal (NL)

( * ) Notice: Subject to any disclaimer, the term of this patent is extended or adjusted under 35 U.S.C. 154(b) by 0 days.

(21) Appl. No.: 11/299,891

(22) Filed: Dec. 13, 2005

(65) Prior Publication Data

US 2006/0203964 A1    Sep. 14, 2006

(30) Foreign Application Priority Data

Dec. 23, 2004    (EP) .................................. 04078493

(51) Int. Cl.
  *A61N 5/10*    (2006.01)
(52) U.S. Cl. ...................................................... 378/65
(58) Field of Classification Search .................. 378/65
  See application file for complete search history.

(56) References Cited

U.S. PATENT DOCUMENTS

| 4,726,046 | A | * | 2/1988 | Nunan .......................... 378/65 |
| 5,027,818 | A | | 7/1991 | Bova et al. |
| 5,291,404 | A | | 3/1994 | Kurokawa et al. |
| 5,317,616 | A | * | 5/1994 | Swerdloff et al. .............. 378/65 |
| 5,528,651 | A | * | 6/1996 | Leksell et al. .................. 378/65 |
| 5,596,653 | A | | 1/1997 | Kurokawa |
| 5,627,367 | A | * | 5/1997 | Sofield ...................... 250/252.1 |
| 6,301,329 | B1 | * | 10/2001 | Surridge ....................... 378/65 |
| 6,345,114 | B1 | * | 2/2002 | Mackie et al. ............... 382/132 |
| 6,459,762 | B1 | * | 10/2002 | Wong et al. ................... 378/65 |
| 6,697,452 | B2 | * | 2/2004 | Xing ............................. 378/69 |
| 6,714,620 | B2 | * | 3/2004 | Caflisch et al. ............... 378/65 |
| 6,882,702 | B2 | * | 4/2005 | Luo .............................. 378/65 |
| 7,046,762 | B2 | * | 5/2006 | Lee .............................. 378/65 |
| 7,289,599 | B2 | * | 10/2007 | Seppi et al. ................... 378/65 |

FOREIGN PATENT DOCUMENTS

EP    1 374 949 A1    1/2004

* cited by examiner

*Primary Examiner*—Allen C. Ho
(74) *Attorney, Agent, or Firm*—Birch, Stewart, Kolasch & Birch, LLP

(57) ABSTRACT

A method for calculating the radiation dose distribution for a radiation treatment system for the purpose of radiation therapy of an animal body, wherein the radiation beam of the radiation treatment system exhibits a specific beam field size and shape at different depths as well as to a device for calculating the radiation dose distribution for a radiation treatment system for the purpose of radiation therapy of an animal body, wherein the radiation beam of the radiation treatment system exhibits a specific beam field size and shape at different depths. The method is characterized by the steps of i) determining at least one beam quality index being representative for the radiation beam being used, and ii) calculating the radiation dose distribution in the specific beam field using parameterized dose deposition kernels based on the at least one beam quality index.

8 Claims, 4 Drawing Sheets

Figure 1:
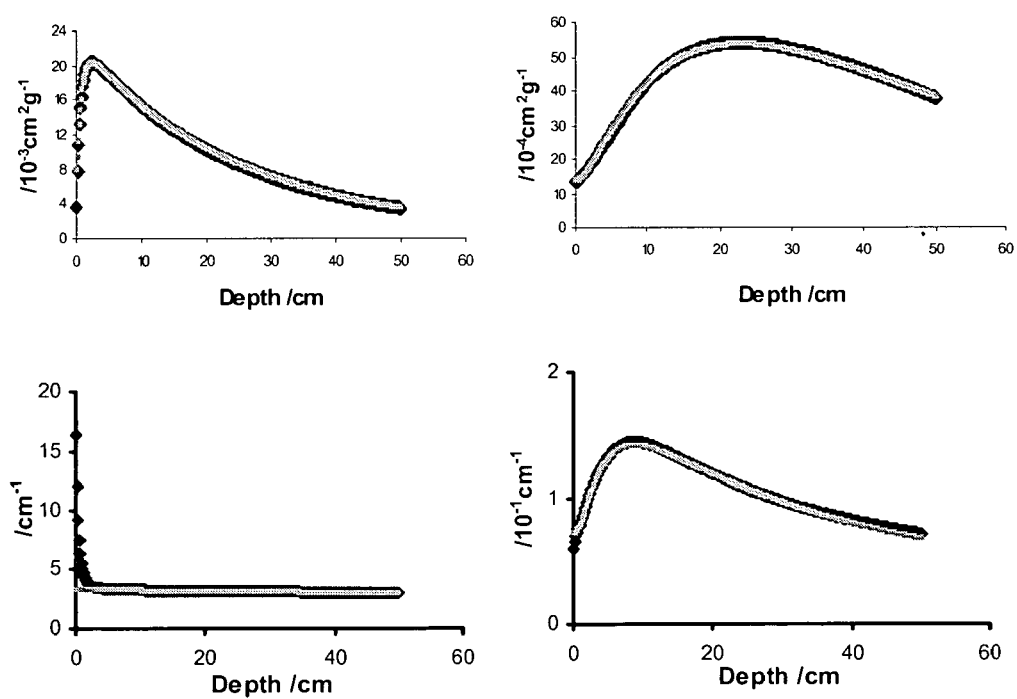

METHOD AND DEVICE FOR CALCULATING THE RADIATION DOSE DISTRIBUTION FOR A RADIATION TREATMENT SYSTEM FOR THE PURPOSE OF RADIATION THERAPY OF AN ANIMAL BODY

The invention relates to a method for calculating the radiation dose distribution for a radiation treatment system for the purpose of radiation therapy of an animal body, wherein said radiation beam of the radiation treatment system exhibits a specific beam field size and shape at different depths.

The invention also relates to a device for calculating the radiation dose distribution for a radiation treatment system for the purpose of radiation therapy of an animal body, wherein said radiation beam of the radiation treatment system exhibits a specific beam field size and shape at different depths.

Calculation accuracy of the radiation dose distribution for the purpose of radiation therapy has been significantly improved during the last decades. The development has gone from simple factor based calculations done manually by clinical physicists to calculations with sophisticated algorithms embedded in commercial treatment planning systems. The present clinical problem is not as much the calculation of the dose distribution, as how to verify the results of the treatment planning system.

The risk for errors in the software used in treatment planning systems increases with the complexity of the algorithms and its applications. There can be bugs in the programming code or errors made by the users. An independent check of the results is desirable/required. In addition, as the accuracy of the treatment planning system improves, the verification mechanism should be able to catch smaller and smaller errors.

The most critical treatment parameter to be checked is the number of monitor units (M) assigned per field (segment) to yield the desired dose. The verification of the number of M for a specific dose can be done using a water phantom geometry, and can be based on tables of measurements, a model, or a combination. The fundamental parameter in the M calculation procedure is the relation between the dose per M to the target and the dose per M to a reference geometry. This relation can include a transition in depth, a change in field size and shape, a wedge, and objects in the field such as blocks and the block holder.

In principle the number of M can be calculated using a factor based model where the number of transitions is e.g. mapped to factors, e.g. tissue phantom ratio (T), a head scatter factor ($S_c$) and a phantom scatter factor ($S_p$). The factors can be tabulated as functions of the field settings, but the irregular shaped fields commonly used impose to large variability to be practically to manage. To make the check applicable for general field shapes some sort of scatter integration must be used.

It is an object of the invention to provide a method and device according to the above allowing the calculation of a radiation dose distribution for a radiation treatment system using a limited amount of data whilst preserving the required accuracy.

According to the invention the method is characterized by the steps of i) determining at least one beam quality index being representative for said radiation beam being used, and
ii) calculating said radiation dose distribution in said specific beam field using parameterized dose deposition kernels based on said at least one beam quality index.

According to an aspect of the invention the method is further characterized by the steps of iii) using for different devices pre-collected measured radiation beam data, said measured radiation beam data comprising:
a) measured phantom dose data at different depths, for different field shapes and sizes and at different energies;
b) calculated dose deposition kernel parameters;
c) measured head scatter factors and output factors that can be transformed into phantom scatter factors for the corresponding field sizes,
iv) determining said at least one beam quality index according to step i) using the pre-collected measured radiation beam data according to step iii);
v) associating the dose deposition kernel parameters to said one or a few beam quality index being determined.

According to a furhter embodiment the method according to the invention is further characterized by the step of vi) using Monte Carlo simulations to simulate said measured data according to step iii).

In a further embodiment the at least one quality index is determined by the ratio between the tissue phantom ratio (TPR) measured at $d_1=20$ cm and $d_2=10$ cm depth ($TPR_{20,10}$).

In another embodiment the at least one beam quality index is determined by the percentage depth dose (PDD) at $d_3=10$ cm ($PDD_{10}$).

In another advantageous embodiment the method according to the invention is characterized in that the dose deposition kernels are pencil dose deposition kernels.

In yet another advantageous embodiment the method according to the invention is characterized in that the dose deposition kernels are point dose deposition kernels.

The device according to the invention further comprising inputting means arranged for inputting at least one beam quality index being representative for said radiation beam being used to calculating means, said calculating means being arranged for calculating said radiation dose distribution using parameterized dose deposition kernels being based on said at least one beam quality index.

In one preferred embodiment the device is a monitor unit (MU) checking device, whereas in another embodiment the device is an IMRT treatment MU checking device.

Figure 2:
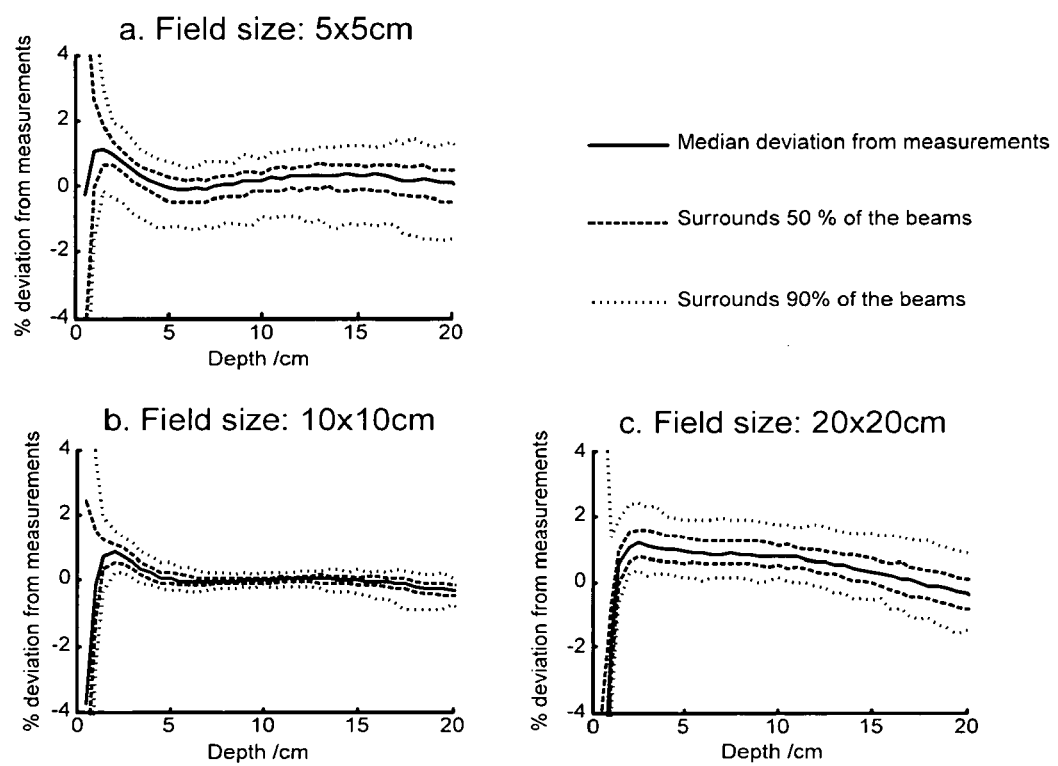
Figure 3:
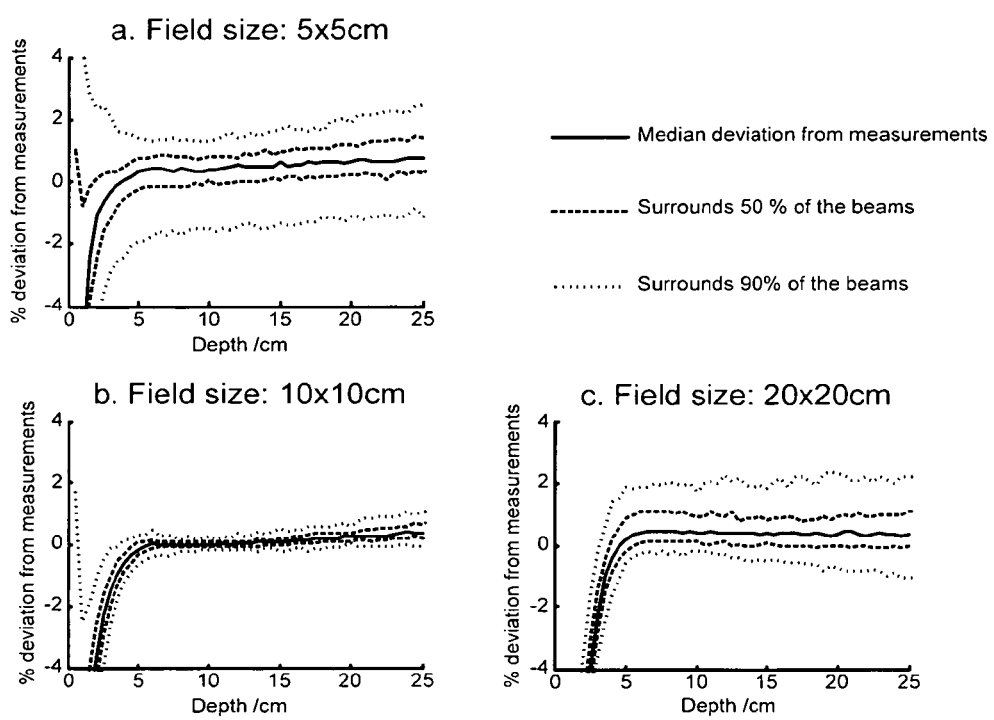
Figure 4:
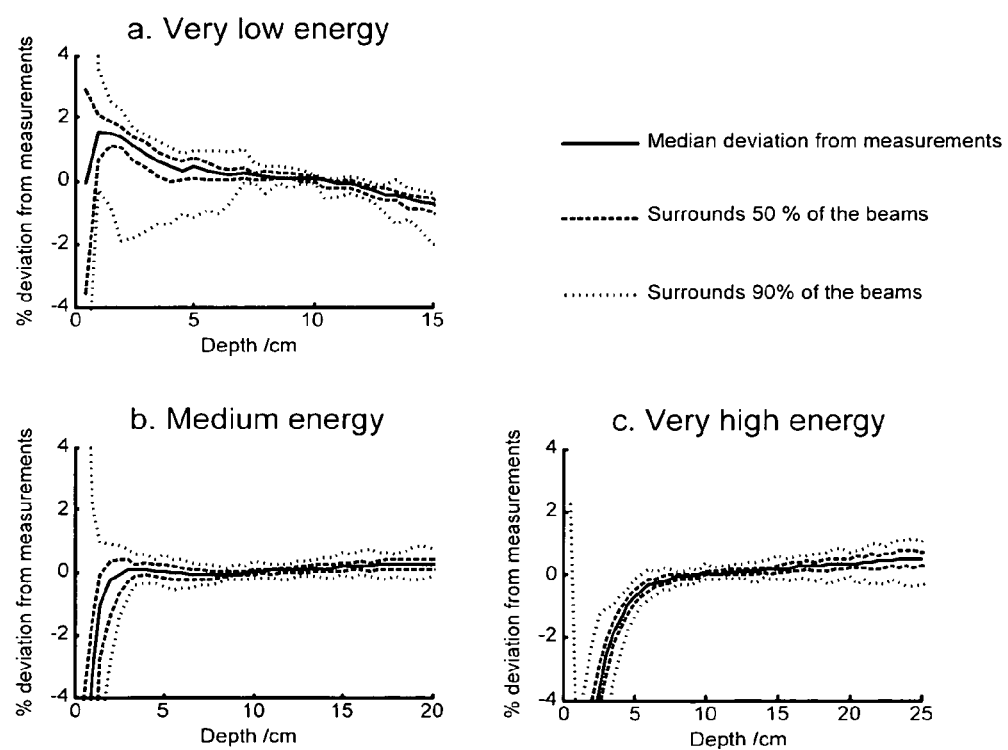

The invention will now be described by means of some examples shown in the accompanying Figures, which show in:

FIG. 1 a comparison between the original tabulated pencil beam parameters and the ones calculated out of equation nos. 3, 4, 5 and 6 for an arbitrary chosen 10 MV accelerator;

FIG. 2 error plots for low energies (210 accelerators), mostly 5 and 6 MV beams, wherein the errors are normalized in a small interval around 10 cm in the 10×10 cm² field;

FIG. 3 error plots for high energies (138 accelerators), mostly 15-18 MV beams, wherein the errors are normalized in a small interval around 10 cm in the 10×10 cm² field; and FIG. 4 error plots for 10×10 cm² fields for very low energy (3-5 MV, 25 accelerators), medium energy (8-10 MV, 173 accelerators) and very high energy (18-25 MV, 88 accelerators), wherein the plots are normalized in a small interval around 10 cm depth.

For implementing the method according to the invention data from different radiation treatment units have been used to determine the calculation model. Each data set for a treatment unit includes depth dose measurements from surface down to 35 cm depth in four field sizes (5×5 cm², 10×10 cm², 15×15 cm² and 20×20 cm²), all with a Source Surface Distance (SSD) equal to 90 cm. Furthermore, measured head scatter factors and output factors are included, which can be transformed into phantom scatter factors for the three field sizes (5×5 cm², 15×15 cm² and 20×20 cm²) at 10 cm depth with a SSD=90 cm. The data collection also includes calculated pencil beam parameters.

For the purpose of deriving the data parameterization according to the invention more than 1000 data sets from around 800 radiation treatment devices were included.

The calculation of $TPR_{20,10}$ is based on the depth dose value at 10 and 20 cm depth. An inverse square correction was done, with the assumption that all the radiation is emitted from the same point (the target). The correction for the changed field size at 20 cm depth was done using the phantom scatter factor for an 11×11 cm field. This value was calculated using a second degree fitting to the phantom scatter factors for 5×5 cm², 10×10 cm², and 15×15 cm² field sizes.

The pencil beam model used from a known commercial treatment planning system is based on a four parameter kernel to describe the primary and scatter part of the dose as a function of the distance to the kernel central axis. Actually three more parameters are used in that treatment planning system to fine tune the fitted results to better conserve the primary/scatter ratio given by the Monte Carlo data and to adjust for small machine individual variations.

In order to construct a simple model, those type of corrections are omitted when implementing the method according to the present invention in a device according to the invention. The kernel value as a function of the distance to the kernel central axis r is expressed as:

$$k(r, z) = \frac{A(z)\exp[-a(z)r] + B(z)\exp[-b(z)r]}{r} \quad (1)$$

where z is the calculation depth and A, B, a, and b are depth dependent parameters. The four parameters are calculated from Monte Carlo simulations with an energy spectra derived from depth dose measurements and measured phantom scatter values. The primary part and the scatter part are separated, such that the first exponential takes care of the primary part and the second takes care of the scatter part.

When the treatment planning system uses the model, the four parameters are tabulated as a function of the depth from 0.075 cm below the surface to below 40 cm, in steps of 0.075 cm.

The kernel as formulated in equation (1) can be integrated over a circular field with radius R to get the dose per energy fluence at the central axis:

$$D(R, z) = 2\pi \int_0^R \Psi(r)k(r, z)r\,dr \quad (2)$$

$$= 2\pi\Psi\left[\frac{A}{a}(z)[1 - \exp[-a(z)R]] + \frac{B}{b}(z)[1 - \exp[-b(z)R]]\right]$$

where the energy fluence is assumed to be constant.

The ratio $2\Pi A/a$ has a clear physical meaning, it describes the primary part of the dose per energy fluence for an infinite field radius. The ratio $2\Pi B/b$ analogously describes the scatter part for an infinite field. Hence, it is more convenient to work with the parameters A/a, B/b, a and b in an attempt to make a depth parameterization, rather then with A, B, a and b directly.

The depth parameterization functions for the primary and scatter part for infinite fields are:

$$\frac{A}{a} = A_1\left[1 - \exp\left[A_2\sqrt{z^2 + A_5^2}\right]\right]\exp[A_3 z + A_4 z^2] \quad (3)$$

and $$\frac{B}{b} = B_1\left[1 - \exp\left[B_2\sqrt{z^2 + B_5^2}\right]\right]\exp[B_3 z + B_4 z^2] \quad (4)$$

where $A_1$, $A_2$, $A_3$, $A_4$, $A_5$, B1, $B_2$, $B_3$, $B_4$ and $B_5$ are fitting parameters. The parameters $A_1$, and $B_1$ are for normalization, and are used to get a correct relation between the primary and scatter part of the dose. The parameter $-A_2$ resembles a linear attenuation coefficient for the primary electrons and $-B_2$ one for the scattered photons. The parameters $-A_3$ and $-B_3$ can be seen as the linear attenuation coefficient for the primary photons.

The parameters $A_4$ and $B_4$ introduce a beam hardening correction. Due to mismatching between the original and the fitted data at shallow depths, we introduced the correction parameters $A_5$ and $B_5$ which have two purposes, they introduce back scattering and slightly extend the build up region. The physical factor that this extension corrects for is the change in mean direction of the secondary particles with depth. At shallow depths the electrons and the scattered photons are more forwardly directed then at deep depths.

The effect on the shape of depth parameterization function for the primary part is limited when $A_5$ is introduced, but for the scatter part the change with $B_5$ is significant. The calculations of the parameters were not done to get the right values according to the interpretations of the parameters. In other words, no effort were made to get, for example, $A_3$ close to the "real" linear attenuation coefficient, the goal was to find the best values of the parameters to fit the functions to the tabled values.

The expression $1-\exp[-a(z)R]$ in equation (2) is the ratio between the primary dose to the central axis with a circular field of radius R and that of an infinite field. This ratio is only weakly depth dependent except in the build-up region, which means that a(z) is only weakly depth dependent. Hence, a is parameterized as a linear function of the depth.

$$a = a_1 + a_2 z \quad (5)$$

where $a_1$ and $a_2$ are fitting parameters.

The expression $1-\exp[-b(z)R]$ in equation (2) can analogously be interpreted as the ratio between the scatter dose to the central axis with a circular field of radius R and an infinite field. It turned out that it was possible to use the same fitting function for b as for A/a and B/b.

$$b = b_1\left[1 - \exp\left[b_2\sqrt{z^2 + b_5^2}\right]\right]\exp[b_3 z + b_4 z^2] \quad (6)$$

where $b_1$, $b_2$, $b_3$, $b_4$ and $b_5$ are fitting parameters.

The parameters of the chosen functions were fitted to the tabulated data extracted from the database containing said pre-measured radiation beam data for all the radiation treatment systems and energies. The fitting step was performed in a stepwise procedure using a script written specially for this purpose. The parameters $A_3$ and $A_4$ were determined from the slope at great depths, $A_2$ was set to get the maximum point at the right position, $A_1$, was set to yield a correct value at 10 cm depth, and $A_5$ to minimize the error just below the surface.

The same method was used for B/b and b, except that $B_3$ was set equal to $A_3$ and $B_4$ equal to $A_4$. The parameters $a_1$ and $a_2$ was found using least square fitting below the build up region for the primary part.

The disagreement between the fitted curve and the a data (FIG. 1) at shallow depths are not very critical since the model is not intended to be used at shallow depth due to the electron contamination problem. The parameterization of b starts to disagree at depths somewhere between 30 cm and 40 cm, which are deeper than for normal treatments.

The seventeen accelerator and energy specific parameters are not explicitly measurable, which means they have to be related to some measurable quantity or calculated through fitting of the entire model against measurements. The first way is preferable, if the precision allows it, as it does not demand a large quantity of measured data for each accelerator and energy. It turned out that the parameters could be calculated with good precision as polynomial functions of the beam quality index $TPR_{20,10}$.

The parameters in the polynomial functions were adjusted to minimize the deviation between the model and depth doses calculated with the original pencil beam parameters.

The model was tested as a predictor of the ratio between the dose at the central axis for different depths and field sizes and the dose to a reference point (a $10 \times 10 \, cm^2$ field at 10 cm depth with SSD=90 cm):

$$D_{ratio}(z,s) = \frac{D(z,s)}{D(z_{ref}, s_{ref})} \quad (7)$$

$$= \left[\frac{SSD + z_{ref}}{SSD + z}\right]^2 \frac{2\pi \int_0^{R(z,s)} k(r, z, TPR_{20.10}) r \, dr}{2\pi \int_0^{R(z_{ref}, s_{ref})} k(r, z, TPR_{20.10}) r \, dr}$$

where k $(r, z, TPR_{20,10})$ is the pencil beam kernel according to equation (1) with a $TPR_{20,10}$ dependence. The integration limit R(z,s) is calculated as a function of the side length s of the square fields and of the depth $$R(z,s) = 0.561 \left[\frac{SSD + z}{SSD + z_{ref}}\right] s \quad (8)$$

where the constant factor is from the relation between square fields and their equivalent circular fields.

The great number of measurements within the data set has made it possible to make reliable estimations of the expected deviations between clinical measurements and the model. FIGS. 2, 3, 4 give the median deviation, surrounded by indicators that delimit 50% and 90% of the accelerators. The accelerators are divided in 5 groups depending on their $TPR_{20,10}$ ratio:

I Very low energy–$TPR_{20,10}$=[0.61, 0.645]
II Low energy–$TPR_{20,10}$=[0.645, 0.682]
III Medium energy–$TPR_{20,10}$=[0.682, 0.744]
IV High energy–$TPR_{20,10}$=[0.744, 0.772]
V Very high energy–$TPR_{20,10}$=[0.772, 0.81]

Systematic deviation between model and data can be visualized by the median error in FIGS. 2, 3 and 4, while the random error can be visualized by the width of the 50% and 90% confidence intervals in the same plots. Both types of errors can originate from both the measurements and the model itself. Systematic errors in measured data will not be considered further in this discussion as the data were acquired by different researchers independently and with varying equipment.

Lack of modelling for electron contamination is the reason for the underestimation of the dose for shallow depths at high energies while shape limitations is likely the reason for the slight overestimation of the phantom scatter factors by up to 1% for practically all field sizes that differ from $10 \times 10 \, cm^2$. This effect is present for all energies but is most significant for the lowest energies.

The device is based on the assumption that the difference in dose distribution between two beams with the same $TPR_{20,10}$ is small. Analysis of the error plots indicates that this assumption is true. The width of the confidence intervals originates from both individuality between accelerators with the same $TPR_{20,10}$, and from random errors in measurements. The dose data stems from three different measurements, i.e. depth dose, output factors in water, and output factors in air, all contributing to the random error of measured data.

The magnitude of the depth dose error can be estimated from the error plots for $10 \times 10 \, cm^2$ fields (FIGS. 2b, 3b, 4a-c). The plots are normalized in a small interval around 10 cm depth and the width of the confidence intervals just around this interval is mainly due to random errors. With this width subtracted it is possible to conclude that the individuality of the accelerators with respect to depth doses has the magnitude of tenth of a percent (except for shallow depths, and very low energies). It is more difficult to draw any conclusions of the degree of individuality in the field size dependence, as no measurements just around the $10 \times 10$ cm field were available.

But the fact that the width of the confidence intervals for $5 \times 5 \, cm^2$, $15 \times 15 \, cm^2$ and $20 \times 20 \, cm^2$ fields do not differ more than they do, indicates that the random errors in the measurements are the main contributor to the spread in the plots. One can also draw a conclusion about the poor quality of $TPR_{20,10}$ as a predictor of dose calculation parameters for shallow depths and very low energies. In these cases a distinct depth dependence of the random deviations between the calculated and measured dose can be seen, but the effect of electron contamination and increasing random error in the depth dose measurements at shallow depths should also be taken into account. $TPR_{20,10}$ as beam quality parameter with shallow depth aspects have been previously discussed, but in another context.

From FIG. 4a it seems that the model is less accurate at very low energies showing both systematic and random deviations from the measurements. It should be noticed that the number of accelerators in the group with very low energy is much smaller than in the other groups and at least the 90% confidence interval is based on too few accelerators to be reliable.

The design of the model does also allow varying beam quality specifications as all parameters are expressed through μ, which absolute value is close to the linear attenuation coefficient. By adjusting μ and make it a function of the position in the field, it would be possible to make a first order correction for off axis softening, or beam hardening due to a metal wedge.

It surprisingly appeared that when using the method according to the invention $TPR_{20,10}$ is useful as a predictor of dose calculation parameters at depths deeper than the range of contaminating electrons.

The pencil beam model with parameterized depth dependence according to the method and device of the present invention fulfills the requirements for a monitor unit verification tool for modern radiotherapy. With a calculation software using an integration algorithm, the central axis doses can be calculated with an accuracy of 2% (disregarding head scatter) for arbitrary field shapes and depths within certain limits.

The method according to the invention is tested for field sizes between $5 \times 5$ cm$^2$ and $20 \times 20$ cm$^2$. The depth should be deeper than the range of contaminating electrons. In most cases, the error will be smaller. The reliability of the given number of monitor units or of the dose can be presented together with the result. This quality can be useful in the clinical work, even at other occasions than verification.

The invention claimed is:

1. A method for calculating a radiation dose distribution of a radiation beam for a radiation treatment system for the purpose of radiation therapy of an animal body, wherein said radiation beam of the radiation treatment system exhibits a size and a shape of a specific beam field at different depths, wherein the method is characterized by the steps of:
   i) determining one beam quality index being representative for said radiation beam being used, and
   ii) calculating said radiation dose distribution in said specific beam field using parameterized dose deposition kernels based on said one beam quality index;
   iii) using for different devices pre-collected measured radiation beam data, said measured radiation beam data comprising:
      a) measured phantom dose data at different depths, for different field shapes and sizes and at different energies;
      b) calculated dose deposition kernel parameters;
      c) measured head scatter factors and output factors that are transformable into phantom scatter factors for the corresponding field sizes,
   iv) determining said one beam quality index according to step i) using the pre-collected measured radiation beam data according to step iii);
   v) expressing the dose deposition kernel parameters as a mathematical function of said one beam quality index being determined.

2. The method according to claim 1, further characterized by step vi) using Monte Carlo simulations to simulate said measured radiation beam data according to step iii).

3. The method according to claim 1, further characterized in that said one beam quality index is determined by a ratio (TPR$_{20,10}$) between a tissue phantom ratio (TPR) measured at d$_1$=20 cm and a tissue phantom ratio (TPR) measured at d$_2$=10 cm depth.

4. The method according to claim 1, further characterized in that said at least one beam quality index is determined by the percentage depth dose (PDD) at d$_3$=10 cm (PDD$_{10}$).

5. The method according to claim 1, further characterized in that the dose deposition kernels are pencil dose deposition kernels.

6. The method according to claim 1, further characterized in that the dose deposition kernels are point dose deposition kernels.

7. The method according to claim 1, characterized in that a dose per energy fluence at the central axis of the radiation beam is determined as:

$$\frac{D}{\Psi(r=0)} \propto 2\pi \int_0^R r \frac{\Psi(r)}{\Psi(r=0)} k(r,z) \, dr \quad (7a)$$

with $$k(r,z) = \frac{A(z)\exp[-a(z)r] + B(z)\exp[-b(z)r]}{r} \quad (7b)$$

wherein the parameters are defined as:

$$\frac{A}{a} = A_1\left[1 - \exp\left[A_2\sqrt{z^2 + A_5^2}\right]\right]\exp[A_3 z + A_4 z^2] \quad (7c)$$

and $$\frac{B}{b} = B_1\left[1 - \exp\left[B_2\sqrt{z^2 + B_5^2}\right]\right]\exp[B_3 z + B_4 z^2] \quad (7d)$$

and $$a = a_1 + a_2 z \quad (7e)$$

and where $$b = b_1\left[1 - \exp\left[b_2\sqrt{z^2 + b_5^2}\right]\right]\exp[b_3 z + b_4 z^2]. \quad (7f)$$

8. The method according to claim 7, characterized in that the parameters are expressed through μ, which is a function of TPR (d$_2$, d$_1$) (TPR$_{20,10}$) with the following expressions:

μ=−0.363009·TPR$_{20,10}$$^3$+0.709250·TPR$_{20,10}$$^2$−0.259794·TPR$_{20,10}$−0.090314

$A_1$=−0.0042·μ$^3$−0.46571·μ$^2$−0.099992·μ+0.0002918

$A_2$=−1605.6·μ$^2$−64.40·μ−1.239

$A_3$=−0.016·μ$^4$−0.0055·μ$^3$−0.01246·μ$^2$+0.991726·μ+0.0002103

$A_4$=0.007·μ$^3$0.1081·μ$^2$0.01211·μ−0.000208

$A_5$=0.003·μ$^2$0.805·+0.23061

$a_1$=−2852·μ$^3$+1641·μ$^2$+47.00·μ+2.007

$a_2$=−0.010·μ−0.016

$B_1$=−69680.47·μ$^4$−12517.918·μ$^3$−780.2216·μ$^2$−20.948788·μ−0.20531052

$B_2$=−16.675·μ$^2$−2.0546·μ−0.06840

$B_3$=1.0011·μ+8.1·10$^{-5}$ $B_4$=0.0033·μ$^3$−0.11080·μ$^2$−0.012183·μ−0,0002067

$B_5$=2290·μ$^2$+225.17·μ+7.084

$b_1$=5415900·μ$^5$+1573050·μ$^4$+180100.6·μ$^3$+10207.44·μ$^2$+285.8012·μ+3.35788

$b_2$=−267.83·μ$^2$−26.215·μ−0.93285

$b_3$=462400·μ$^5$+87700·μ$^4$+5070.5·μ$^3$+9.641·μ$^2$−6.3843·μ−0.15488

$b_4$=−12319·μ$^5$+2953.1·μ$^4$−263.64·μ$^3$−10.2445·μ$^2$−0.158854·μ−0.0003494 and $b_5$=14.15·μ+1.17168.

* * * * *